United States Patent
Kurata et al.

(10) Patent No.: US 6,593,510 B2
(45) Date of Patent: Jul. 15, 2003

(54) WATER-DECOMPOSABLE ABSORBENT ARTICLE

(75) Inventors: Nobuhiro Kurata, Kagawa (JP); Mitsuhiro Wada, Kagawa (JP); Yuka Miyazaki, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 91 days.

(21) Appl. No.: 09/749,368

(22) Filed: Dec. 22, 2000

(65) Prior Publication Data

US 2001/0008964 A1 Jul. 19, 2001

(30) Foreign Application Priority Data

Jan. 6, 2000 (JP) ........................................ 2000-000576

(51) Int. Cl.⁷ ................................................ A61F 13/15
(52) U.S. Cl. ........................ 604/364; 604/365; 604/367
(58) Field of Search ................................ 604/364, 365, 604/367

(56) References Cited

U.S. PATENT DOCUMENTS

| | | | |
|---|---|---|---|
| 2,890,700 A | | 6/1959 | Lönberg-Holm ............ 128/284 |
| 3,563,241 A | * | 2/1971 | Evans ......................... 128/284 |
| 3,575,173 A | * | 4/1971 | Loyer ......................... 128/290 |
| 3,636,952 A | | 1/1972 | George ....................... 128/287 |
| 3,727,615 A | * | 4/1973 | Duchane ..................... 128/290 |
| 3,804,092 A | * | 4/1974 | Tunc ........................... 128/284 |
| 3,881,487 A | | 5/1975 | Schrading ................... 128/284 |
| 4,002,171 A | * | 1/1977 | Taft ............................. 128/284 |
| 4,537,807 A | * | 8/1985 | Chan et al. .................. 428/74 |
| 5,190,533 A | * | 3/1993 | Blackburn .................. 604/367 |
| 5,207,662 A | * | 5/1993 | James ........................ 604/385.2 |
| 5,300,358 A | * | 4/1994 | Evers .......................... 428/286 |
| 5,613,959 A | * | 3/1997 | Roessler et al. ............ 604/364 |
| 5,681,299 A | * | 10/1997 | Brown ........................ 604/364 |
| 5,722,966 A | * | 3/1998 | Christon et al. ............ 604/364 |
| 5,763,044 A | * | 6/1998 | Ahr et al. .................... 428/131 |
| 5,800,377 A | * | 9/1998 | Campion et al. ............ 604/13 |
| 5,980,500 A | * | 11/1999 | Shimizu et al. ............ 604/385.1 |
| 6,087,550 A | * | 7/2000 | Anderson-Fischer et al. .... 604/364 |
| 6,127,593 A | * | 10/2000 | Bjorkquist et al. .......... 604/364 |
| 6,384,297 B1 | * | 5/2002 | Colman et al. .............. 604/364 |

FOREIGN PATENT DOCUMENTS

| | | |
|---|---|---|
| JP | 08-019571 | 1/1996 |
| JP | 08-038547 | 2/1996 |
| WO | WO98/08475 | 3/1998 |

* cited by examiner

*Primary Examiner*—Weilun Lo
*Assistant Examiner*—Jacqueline F Stephens
(74) *Attorney, Agent, or Firm*—Darby & Darby

(57) ABSTRACT

Provided is a water-decomposable absorbent article including a water-decomposable back layer, a water-decomposable and liquid-pervious surface layer, and a water-decomposable absorbent layer sandwiched between the back layer and the surface layer. The absorbent article includes an outer peripheral region being formed in a predetermined width spaced from a peripheral edge of the absorbent article, and an inner region located inside the outer peripheral region. The absorbent layer and the back layer, and/or the absorbent layer and the surface layer are bonded to each other with a water-soluble or water-swellable adhesive therebetween in the inner region, and the interlayer bonding strength of the layers bonded with the adhesive in the inner region is higher than the interlayer bonding strength of the layers in the outer peripheral region, both in wet and in dry.

9 Claims, 3 Drawing Sheets

WATER-DECOMPOSABLE ABSORBENT ARTICLE

BACKGROUND OF THE INVENTION

1. Field of the Invention

The present invention relates to a water-decomposable absorbent article for sanitary napkins, pantiliners, incontinence pads, diapers, etc.

2. Description of the Related Art

Recently, absorbent articles disposable in flush toilets have come available, including, for example, sanitary napkins, pantiliners, incontinence pads, diapers, etc. For example, Japanese Unexamined Patent Publication (Kokai) Nos. Heisei 8-38547 and 8-19571 disclose water-decomposable absorbent articles comprising a water-decomposable absorbent layer, and water-decomposable surface and back layers between which the absorbent layer is sandwiched.

In these water-decomposable absorbent articles, the constituent layers are relatively firmly bonded to each other so as to prevent the articles from being loosened or broken to lose their shape during use. However, in case where the layers constituting them are bonded to each other with a high-strength adhesive, the absorbent articles used could not be readily decomposed in water in toilets. This is because the constituent layers could not be readily separated from each other in toilets, and therefore they will float in septic tanks and drains owing to air existing between respective constituent layers, and could not disperse in water. On the other hand, however, in case where the constituent layers are bonded to each other by lower bonding strength so as to ensure their decomposition in water, the absorbent articles will be loosened and could not keep their shape during use.

SUMMARY OF THE INVENTION

An object of the present invention is to provide a water-decomposable absorbent article which can surely keep its shape during use and can be easily decomposed in water when disposed of in toilets after use.

According to an aspect of the invention, a water-decomposable absorbent article may comprise a water-decomposable back layer, a water-decomposable and liquid-pervious surface layer, and a water-decomposable absorbent layer sandwiched between the back layer and the surface layer, wherein;

the absorbent article including an outer peripheral region being formed in a predetermined width spaced from a peripheral edge of the absorbent article, and an inner region located inside the outer peripheral region, the absorbent layer and the back layer, and/or the absorbent layer and the surface layer are bonded to each other with a water-soluble or water-swellable adhesive therebetween in the inner region, and the interlayer bonding strength of the layers bonded with the adhesive in the inner region is higher than the interlayer bonding strength of the layers in the outer peripheral region, both in wet and in dry.

In this, the interlayer peeling rate of the constituent layers in wet may be higher in the outer peripheral region than in the inner region.

The absorbent article of the invention is so constituted that its interlayer bonding strength is higher in the inner region than in the outer peripheral region both in dry and in wet. Being so constituted, the constituent layers are hardly separated from each other and are hardly loosened both in dry and in wet while the absorbent article is used. Accordingly, the absorbent article well keeps its shape during use and is highly durable. In addition, the absorbent article is so specifically constituted that, while in wet, the interlayer bonding force in the outer peripheral region is low and the interlayer peeling rate is higher in the outer peripheral region than in the inner region. Therefore, when the absorbent article is, after used, disposed of in flush toilets, the constituent layers are readily separated from each other first in the outer peripheral region. As a result, air existing inside the inner region moves away through the thus-separated layers in the outer peripheral region to prevent the absorbent article from floating in septic tanks. Even though the interlayer bonding strength in the inner region is high and the constituent layers therein will be peeled slowly in wet, the interlayer peeling in the inner region can be promoted as triggered by interlayer peeling in the outer peripheral region, when the absorbent article sank in septic tanks. As a result, the absorbent article disposed of in toilets can be smoothly decomposed.

For example, the outer peripheral region has a width of from 2 to 25 mm inwardly from a peripheral edge of the absorbent article. The inner region is meant to indicate the region except for the outer peripheral region, and an adhesive is partially applied to the inner region.

In the outer peripheral region, the constituent layers are bonded to each other with a water-soluble adhesive therebetween, and the solubility in water of the adhesive in the inner region is preferably lower than that of the adhesive in the outer peripheral region.

In the outer peripheral region, the constituent layers are bonded to each other with a water-soluble adhesive therebetween, and the amount of the water-soluble adhesive applied to the unit area of the inner region may be larger than that of the adhesive applied to the unit area of the outer peripheral region.

In that case, the adhesives applied to the inner region and to the outer periphery region may be each made of preferably polyvinyl alcohol, and the applied amount may fall between 10 and 30 g/m$^2$ in the outer peripheral region and the applied amount may fall between 30 and 200 g/m$^2$ in the inner region.

In the absorbent article of the invention, the constituent layers in the outer peripheral region may be bonded to each other under pressure without interposing the adhesive. For example, in the outer peripheral region, the constituent layers may be bonded to each other via hydrogen bonding.

DESCRIPTION OF THE PREFERRED EMBODIMENTS

Figure 1:
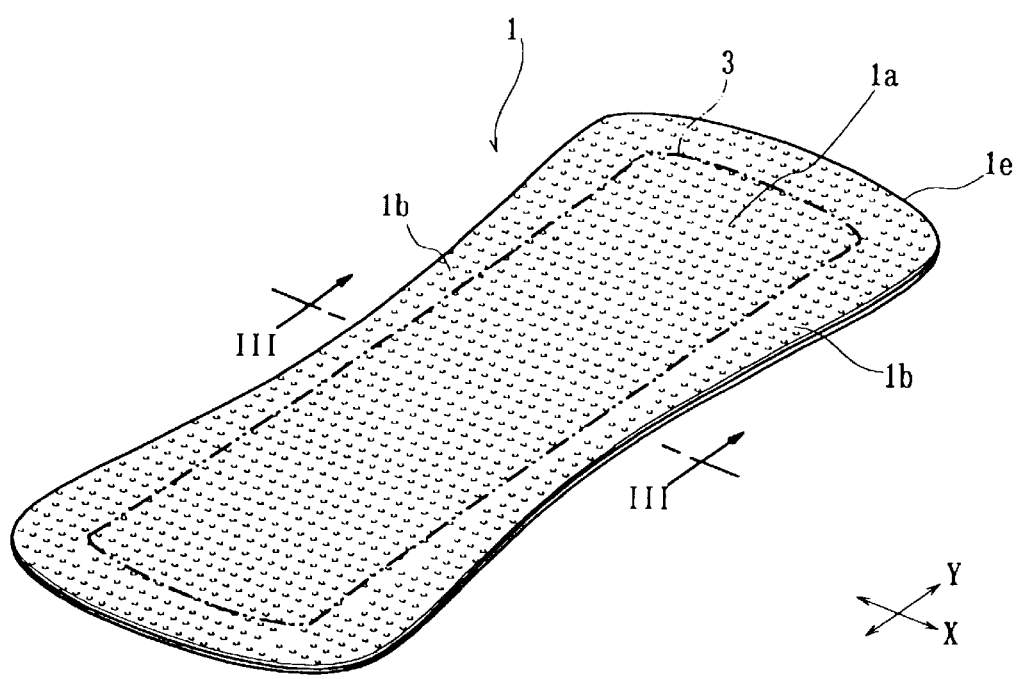
FIG. 1 is a perspective view of one embodiment of an absorbent article according to the invention.
Figure 2:
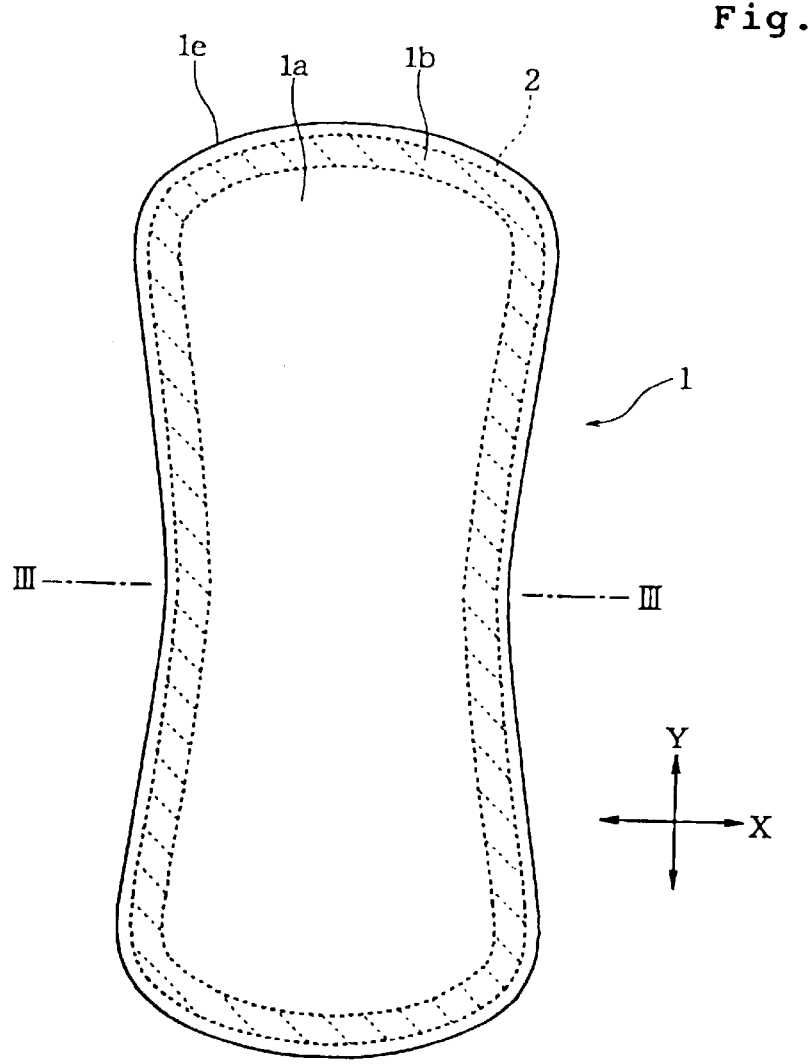
FIG. 2 is a plan view of the absorbent article of FIG. 1.
Figure 3:
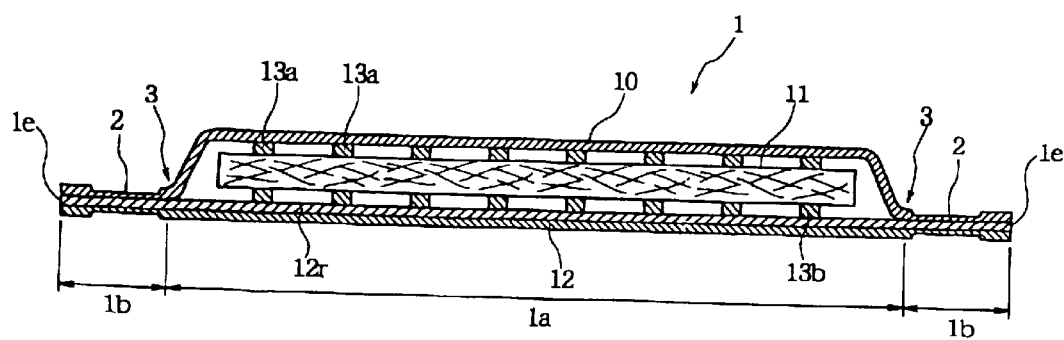
FIG. 3 is a cross-sectional view of the absorbent article of FIG. 1 and FIG. 2, cut along the line III—III.

The invention is described in detail with reference to the accompanying drawings. FIG. 1 is a perspective view of one embodiment of the absorbent article according to the invention, looking from a top surface thereof (this top surface serves as a body facing surface); FIG. 2 is a plan view of the absorbent article of FIG. 1, looking from the top surface thereof; FIG. 3 is a cross-sectional view of the absorbent article of FIG. 1 and FIG. 2, cut along the line III—III. In these drawings, the longitudinal direction of the absorbent article illustrated is designated by Y, and the transverse direction nearly perpendicular to the direction Y is designated by X.

The absorbent article of the invention shown in FIG. 1 and FIG. 2 is for pantiliners or sanitary napkins, and this is decomposable in water. As shown in FIG. 3, the absorbent article 1 comprises a water-decomposable and liquid-pervious surface layer 10 that serves as the body facing surface, a water-decomposable back layer 12, and a water-decomposable absorbent layer 11 sandwiched between the surface layer 10 and the back layer 12. Furthermore, a thermoplastic resin layer 12r is provided between the back layer 12 and the absorbent layer 11.

In an outer peripheral region 1b of the absorbent article 1 that extends in a predetermined width from a peripheral edge 1e to a boundary 3 thereof, only the surface layer 10 and the back layer 12 are laminated. In the outer peripheral region 1b, the surface layer 10 and the back layer 12 are heat-sealed under pressure to envelop the absorbent layer 11. Concretely, in this region, the surface layer 10 and the back layer 12 are heat-sealed with the water-soluble thermoplastic resin layer 12r disposed and fused between them to form a round-seal portion 2 in which the surface layer 10 and the back layer 12 are bonded to each other.

In the inner region 1a surrounded by the outer peripheral region 1b, the surface layer 10 and the absorbent layer 11 are bonded to each other with a water-soluble or water-swellable adhesive 13a provided therebetween, and the back layer 12 and the absorbent layer 11 are also bonded to each other with a water-soluble or water-swellable adhesive 13b. In the inner region 1a, the adhesives 13a and 13b are spirally or spotwise applied to partially bond the surface layer 10 to the absorbent layer 11, and to partially bond the surface layer 12 to the absorbent layer 11.

The bonding strength between the surface layer 10 and the absorbent layer 11 and that between the absorbent layer 11 and the back layer 12 in the inner region 1a are higher than the bonding strength between the surface layer 10 and the back layer 12 in the round-seal portion 2 in the outer peripheral region 1b. Accordingly, while the absorbent article 1 is used, its constituent layers in the inner region 1a are hardly peeled, and, as a result, the absorbent article 1 well keeps its shape in the region 1a and is hardly loosened or broken during use. Even in wet, the interlayer bonding strength in the inner region 1a is kept higher than that in the outer peripheral region 1b. Therefore, even after body fluid having passed through the surface layer 10 has reached the absorbent layer 11, the constituent layers are still hardly peeled in the inner region 1a, and the thus-wetted absorbent article 1 can well keep its shape.

On the other hand, in the outer peripheral region 1b, the interlayer bonding force is low, and the interlayer peeling rate in wet is higher in the outer peripheral region 1b than in the inner region 1a. Therefore, when the absorbent article 1 is, after used, disposed of in toilets and led to septic tanks, the constituent layers in the outer peripheral region 1b thereof are readily and immediately peeled by a large amount of water thereon. With that, water immediately penetrates into the interface between the outer layer 10 and the absorbent layer 11 and the interface between the absorbent layer 11 and the back layer 12 in the inner region 1a to remove air existing between them, whereby the absorbent article 1 can readily sink in septic tanks. After having sunk in septic tanks, the absorbent article 1 receives a large amount of water in its inner region 1a. Accordingly, even if the solubility in water of the adhesives 13a and 13b in the inner region 1a is poor, the interlayer peeling of the constituent layers in the region 1a are promoted by such a large amount of water, and, as a result, the absorbent article 1 is readily decomposed in water.

Preferably, the width of the outer peripheral region 1b, that is, the distance between the peripheral edge 1e and the boundary 3 is from 2 to 25 mm, more preferably from 8 to 20 mm. If the width is larger than the uppermost limit of the defined range, the inner region 1a could not have the necessary interlayer bonding strength, and the self-retention of the absorbent article 1 will be poor. On the other hand, if the width is smaller than the lowermost limit of the defined range, or that is, if the inner region 1a having a high interlayer bonding strength is too adjacent to the peripheral edge 1e, the decomposability in water of the absorbent article 1 will be low, and, in addition, the absorbent article 1 will give a rough feel to the skin of a wearer.

The round-seal portion 2 may be formed to cover the entire width of the outer peripheral region 1b, or, as the case may be, the width of the round-seal portion 2 in the outer peripheral region 1b may be smaller than the width of the outer peripheral region 1b, as shown in FIG. 2. The round-seal portion 2 may be endlessly formed to run along the entire periphery of the absorbent article, or may be formed in both side edges lying opposite one another in the direction X of the absorbent article. The width of the round-seal portion 2 may fall, for example, between 1 and 4 mm or so. As the case may be, the round-seal portion may be in the form of discontinuous strips running along the periphery of the absorbent article.

In the inner region 1a, the adhesives 13a and 13b may be spirally or spotwise dispersed at intervals throughout the entire interspace between the respective layers. If so, water could easily penetrate into the interface between the surface layer 10 and the absorbent layer 11 and the interface between the absorbent layer 11 and the back layer 12 when the constituent layers in the outer peripheral region 1b are peeled in septic tanks and others, and the inner region 1a will be more readily decomposed in water.

In order that the interlayer bonding strength of the round-seal portion 2 in the outer peripheral region 1b is lowered and the interlayer peeling rate in wet in the outer peripheral region 1b is increased, while the interlayer bonding strength in the inner region 1a is made higher than that in the round-seal portion 2 and the interlayer peeling rate in wet in the region 1a is made lower than that in the round-seal portion 2, it is desirable that the water-soluble thermoplastic resin layer 12r for bonding the constituent layers in the round-seal portion 2 differs from the water-soluble or water-swellable adhesives 13a and 13b to be provided in the inner region 1a.

For example, in order to form the round-seal portion 2, the thermoplastic resin layer 12r to be applied to the back layer 12 on the side of the absorbent layer may be a water-soluble polyvinyl alcohol film, and the polyvinyl alcohol film may be laminated on a sheet of water-decomposable fabric or paper that forms the back layer 12. The adhesives 13a and 13b to be provided in the inner region 1a are soluble or swellable in water, and they may be hot-melt adhesives of polyvinyl alcohol.

In case where the water-soluble polyvinyl alcohol is used to form the round-seal portion 2 in the outer peripheral region 1b, the constituent layers in the round-seal portion 2 in the outer peripheral region 1b can be rapidly peeled in septic tanks and others, and, as a result, water can readily penetrate into the inner region 1a from the outer peripheral region 1b, whereby the absorbent article can more readily sink in septic tanks. When the absorbent article thus having sunk in septic tanks receives a large amount of water, the surface layer 10, the absorbent layer 11 and the back layer 12 in the inner region 1a are dispersed in water. Accordingly, even though the adhesives 13a and 13b are swellable in water but are poorly soluble in water, the absorbent article will be soon decomposed in water due to dispersal of the respective constituting layers.

In this case, the degree of saponification and the degree of polymerization of the adhesives 13a and 13b may be varied, whereby the adhesives 13a and 13b could be so controlled that their adhesiveness is higher but their solubility in water is lower than the adhesiveness and the solubility in water of the water-soluble polyvinyl alcohol film as the adhesive in the round-seal portion 2. It is desirable that the adhesives 13a and 13b have a higher adhesiveness but have a lower solubility in water is preferred, since the adhesives 13a and 13b hardly dissolve when the inner region 1a has received body fluid during use of the absorbent article, and the absorbent article can well keep its shape. In septic tanks and others, water having penetrated into the outer peripheral region 1b immediately moves to the inner region 1a to promote the interlayer peeling in the region 1a. The water-soluble adhesives suitable to the adhesives 13a and 13b include, for example, cellulose derivatives such as methyl cellulose, hydroxyethyl cellulose, carboxymethyl cellulose, etc.; water-soluble polymers such as polyvinyl alcohol, sodium alginate, sodium polyacrylate, polyacrylic acid ether, polyvinyl pyrrolidone, isobutylene-maleic anhydride copolymer, etc.; starch, dextrin, etc. Among those, preferred is polyvinyl alcohol.

The adhesive to be used in the round-seal portion 2 and the adhesives 13a and 13b to be applied to the inner region 1a may have generally similar degree of solubility in water, and the amount thereof may be varied to such that the amount of the adhesives in the inner region 1a is larger than that of the adhesive in the round-seal portion 2 to vary the bonding strength between the outer peripheral region 1b and the inner region 1a.

In this case, the amount of a water-soluble polyvinyl alcohol for applying to the adhesives 13a and 13b preferably falls between 30 and 200 g/m$^2$ in terms of a basis weight (actual Metsuke in the bonded area). With their amount falling within the defined range, the adhesives will ensure bonding strength enough for the absorbent article 1 to keep its shape during use. Also preferably, the amount of the polyvinyl alcohol for applying between the surface layer 10 and the back layer 12 in the round-seal portion 2 falls between 10 and 30 g/m$^2$. With its amount falling within the defined range, the round-seal portion 2 in the outer peripheral region 1b ensures rapid interlayer peeling in flush toilets and septic tanks.

The back layer 12 is readily dispersed in water jets in flush toilets or in water in septic tanks, and it may be formed of water-decomposable paper, water-decomposable non-woven fabric or the like that contains water-dispersible fibers. For example, it may be made of (1) a water-decomposable paper sheet of pulp fibers where the pulp fibers are bonded to each other via hydrogen bonding therebetween, (2) a water-decomposable paper sheet of pulp fibers and other water-dispersible fibers of rayon or the like where the constituent fibers are bonded to each other with a water-soluble binder, (3) a water-decomposable paper sheet of water-dispersible fibers where the constituent fibers are simply entangled, or (4) a water-decomposable non-woven fabric of water-dispersible fibers having a relatively short length where the constituent fibers are forcedly entangled through water-jetting treatment. Preferably, the outer surface of the back layer 12 (this outer surface serves as a garment facing face) is coated with a water-soluble resin such as a polyvinyl alcohol, an unsaturated carboxylic acid copolymer or the like. Thus coated, the back layer 12 is preferably impervious to fluid.

The absorbent layer 11 may be made of, for example, water-decomposable paper, pulp or non-woven fabric. For example, air-laid pulp or the like may be formed into the absorbent layer 11 to have a basis weight (a basis weight is also referred to as Metsuke) of from 50 to 70 g/m$^2$ or so. In case where water-decomposable paper is used for forming the absorbent layer 11, it is desirable that a plurality of relatively thin sheets of water-decomposable paper are stacked, since the thus-stacked sheets are well decomposable in water. For example, 4 to 8 sheets of the water-decomposable paper having a basis weight of from 10 to 20 g/m$^2$ are stacked to form the absorbent layer 11. Sheets of the water-decomposable paper coated with a water-swellable resin such as polyvinyl alcohol or the like may be stacked to form the absorbent layer 11.

The surface layer 10 is, for example, made of a water-decomposable non-woven spun lace fabric. A plurality of sheets of the water-decomposable paper may be laminated on a water-decomposable non-woven fabric to form the surface layer 10. In this case, the non-woven fabric and the water-decomposable paper sheets may be integrated via hydrogen bonding or needling. Since the surface layer 10 acts to lead excretions to the underlying absorbent layer 11, it is preferably perforated to have a plurality of perforations throughout the entire area thereof, for example, as shown in FIG. 1.

Figure 4:
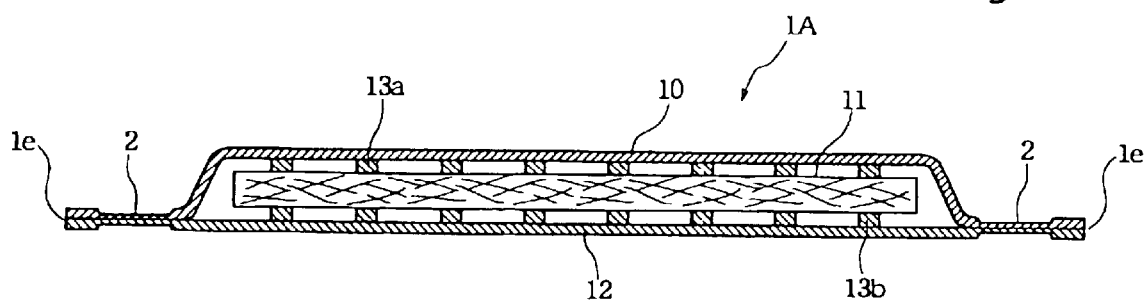
FIG. 4 is a cross-sectional view of another embodiment of the absorbent article according to the invention.

FIG. 4 is a cross-sectional view of another embodiment of the absorbent article according to the invention. The absorbent article 1A of FIG. 4 differs from the absorbent article 1 of FIG. 3 in that the back layer 12 of the former is not coated with the thermoplastic resin layer 12r (this layer is also referred to as a water-soluble adhesive, and it is a water-soluble polyvinyl alcohol film layer, for example). Since the absorbent article 1A of FIG. 4 does not have the resin layer 12r, the surface layer 10 and the back layer 12 in the outer peripheral region 1b therein are directly heat-sealed under pressure under the condition of containing a small amount of water to form the round-seal portion 2 in the outer peripheral region 1b. Accordingly, in the round-seal portion 2 of the absorbent article 1A, the two layers 10 and 12 are directly bonded to each other via hydrogen bonding of the constituent fibers.

The strength of hydrogen bonding is lower than the bonding strength of the adhesive. Therefore, in the absorbent article 1A, the bonding strength between the surface layer 10 and the absorbent layer 11 bonded to each other with the adhesive 13a therebetween in the inner region 1a is higher than the bonding strength between the surface layer 10 and the back layer 12 in the outer peripheral region 1b, as is the case with the absorbent article 1. In the absorbent article of this embodiment, the round-seal portion 2 in which the constituent layers are bonded to each other via hydrogen bonding having lower bonding strength is formed in the outer peripheral region, that is, in a range of from 2 to 25 mm in width, more preferably from 8 to 20 mm in width from the peripheral edge 1e of the absorbent article. In this region, the absorbent article is hardly loosened owing to the movement of a body to which it is fitted. Therefore, since the adhesives 13a and 13b are provided in the inner region 1a in the absorbent article as set forth above, the absorbent article can well keep its shape as a whole, and is hardly loosened, delaminated or broken while it is fitted to the skin of a wearer.

Since the hydrogen bonding in the round-seal portion 2 is rapidly broken immediately after the absorbent article 1A is disposed of in water, water rapidly penetrates into the absorbent article 1A through the outer peripheral region 1b. As a result, the absorbent article 1A is immediately and surely decomposed in water.

Figure 5:
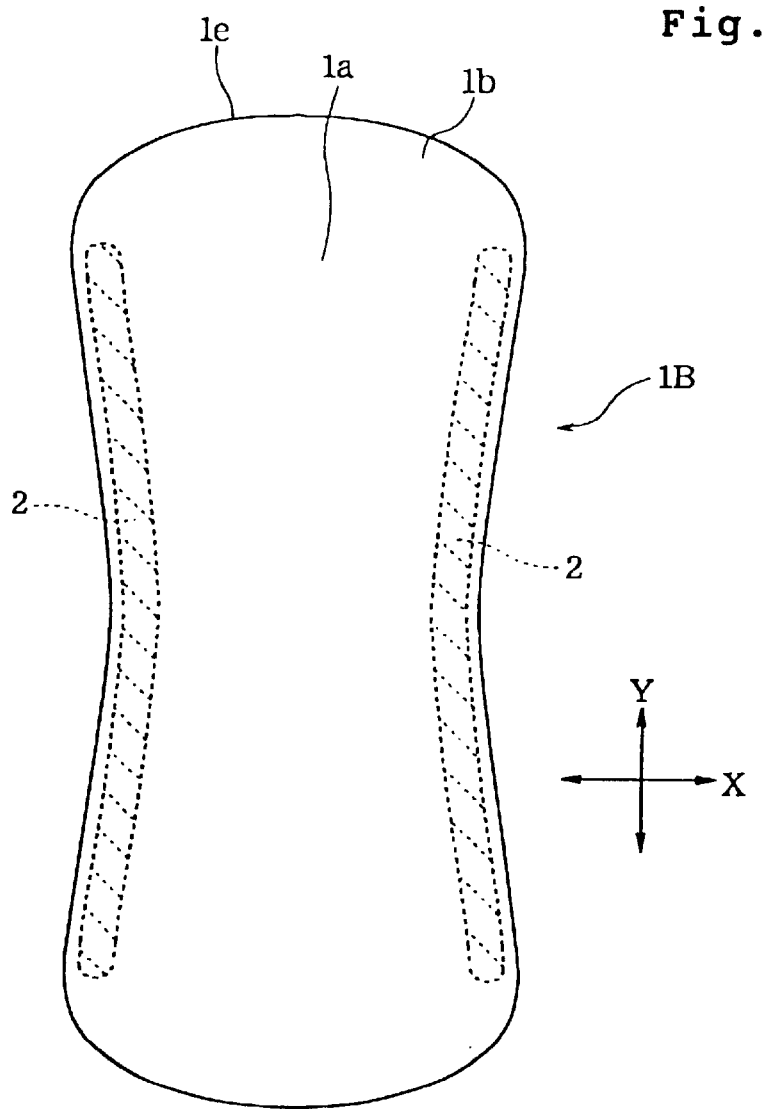
FIG. 5 is a plan view of still another embodiment of the absorbent article according to the invention.

FIG. 5 is a plan view of still another embodiment of the absorbent article of the invention. With the invention, it is not necessary to endlessly provide the round-seal portion 2 along the entire periphery of the absorbent article. As shown in an absorbent article B of FIG. 5, the round-seal portion 2 may be formed in both side edges lying opposite one another in the direction X of the absorbent article. In this case, when the absorbent article 1B is disposed of in water, water rapidly penetrates thereinto through end edges lying opposite one another in the direction Y, and, as a result, the absorbent article 1B is readily decomposed in water. As the case may be, the round-seal portion 2 may be in the form of discontinuous strips.

Preferably, in the invention, the back side of the absorbent article, that is, the outer surface of the back layer 12 (this outer surface serves as a garment facing surface) is entirely coated with an adhesive portion and covered with a release film for protecting the adhesiveness while the absorbent article is not used. Also preferably, the release film is decomposable in water. Still preferably, the package for enveloping the absorbent article is also decomposable in water.

EXAMPLES

The invention is described in more detail with reference to the following Examples, which, however, are not intended to restrict the scope of the invention.

For the examples of the absorbent article according to the invention, pantiliners were prepared as shown in FIG. 3 and FIG. 4. These had a length of 140 mm and a width of 55 mm. For these, the surface layer 10 was made of a non-woven fabric of wet-spun lace, having a basis weight of 45 g/m$^2$; and the absorbent layer 11 was made of a sheet of air-laid pulp, having a basis weight of 60 g/m$^2$.

In Example 2, the back layer 12 was made of a non-woven fabric of wet-spun lace having a basis weight of 45 g/m$^2$, and this was laminated with a water-soluble polyvinyl alcohol film having a basis weight of 30 g/m$^2$ (as shown in FIG. 3 where the back layer 12 is coated with the resin layer 12r).

In Example 1, the back layer 12 was made of a non-woven fabric of wet-spun lace having a basis weight of 45 g/m$^2$, and this was not laminated with the water-soluble polyvinyl alcohol film (as shown in FIG. 4 where the back layer 12 is not coated with the resin layer 12r).

Both in Example 1 and Example 2, the adhesive to be used was a hot-melt adhesive of water-soluble polyvinyl alcohol, and its amount to be coated was 7 g/m$^2$. The adhesive was spirally applied to the absorbent layer 11 to have a cross-section diameter of 18 mm. This was applied thereto only in the inner region of 18×100 mm.

In the outer peripheral region 1b, the constituent layers were heat-sealed under pressure to form the round-seal portion 2 having a width of 5 mm and spaced from the peripheral edge of the pantiliner by 3 mm. The heat-sealing was effected at 120° C. under 3922 kPa for 3 seconds. In Example 2, the outer peripheral region 1b was heat-sealed in the manner as set forth above to form the round-seal portion 2 therein; but in Example 1, the outer peripheral region 1b was not heat-sealed and therefore the round-seal portion was not formed.

The layer constitution in Comparative Examples was the same as in the above-mentioned Examples. In Comparative Example 1, however, the adhesive was not provided in the inner region, and only the round-seal portion having the polyvinyl alcohol film was formed in the outer peripheral region; and in Comparative Example 2, the round-seal portion was not formed, and the constituent layers were bonded to each other with a water-insoluble hot-melt adhesive in the inner region 1a.

The pantiliners thus produced in the Examples and Comparative Examples were subjected to a wear test, a test in a septic tank, and a test for decomposition in water. The data obtained are given in Table 1 below.

Wear Test

The samples were tested by ten panelists. After used, the condition of each sample was macroscopically checked. In Table 1, "○" indicates that the tested samples were not broken; and "x" indicates that the tested samples were broken.

Test in Septic Tank

The samples were disposed of in a flush toilet and led to a septic tank. In the septic tank, the behavior of each sample was macroscopically checked. In Table 1, "○" indicates that the samples were pulverized into individual layers immediately when led into the septic tank; and "x" indicates that the samples were not separated into individual layers.

Test for Decomposition in Water

The samples were tested according to the water-decomposability test in JIS P-4501. Precisely, each sample was cut to have a length of 10 cm and a width of 10 cm, put into a 300 ml beaker filled with 300 ml of ion-exchanged water, and stirred therein with a stirrer. The revolution of the stirrer was 600rpm. While stirred, the sample was periodically checked, and the time taken by it until its dispersion in water was recorded. In Table 1, "○" indicates that the samples were decomposed in water within 100 seconds; and "x" indicates that the samples were not decomposed in water.

TABLE 1

|  | Example 1 | Example 2 | Comparative Example 1 | Comparative Example 2 |
| --- | --- | --- | --- | --- |
| Adhesive between Surface Layer and Absorbent Layer | Yes | Yes | No | Yes (water-insoluble adhesive) |
| Adhesive between Absorbent Layer and Back Layer | Yes | Yes | No | Yes (water-insoluble adhesive) |
| Resin Layer Laminated on Back Layer | No | Yes | Yes | No |

TABLE 1-continued

|  | Example 1 | Example 2 | Comparative Example 1 | Comparative Example 2 |
|---|---|---|---|---|
| Round-Seal Portion | No | Yes | Yes | No |
| Wear Test | ○ | ○ | x | ○ |
| Test in Septic Tank | ○ | ○ | x | x |
| Test for Decomposition in Water | ○ | ○ | ○ | x |

As set forth above, the layers constituting the water-decomposable absorbent article of the invention are hardly separated from each other while the absorbent article is fitted to the skin of the wearer, and therefore the absorbent article has high self-retention and high durability during use. Furthermore, when disposed of in flush toilets, the constituent layers of the absorbent article can be readily separated from the outer peripheral region thereof, so that the absorbent article is readily and surely decomposed in water.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. A water-decomposable absorbent article comprising a water-decomposable back layer, a water-decomposable and liquid-pervious surface layer, and a water-decomposable absorbent layer sandwiched between the back layer and the surface layer, wherein;

the absorbent article including an outer peripheral region being formed in a predetermined width spaced from a peripheral edge of the absorbent article, and an inner region located inside the outer peripheral region, the absorbent layer and the back layer, and/or the absorbent layer and the surface layer are bonded to each other with a water-soluble or water-swellable adhesive therebetween in the inner region, and an interlayer bonding strength of the layers bonded with the adhesive in the inner region is higher than the interlayer bonding strength of the layers in the outer peripheral region, when both wet and dry, and wherein constituent layers in the outer peripheral region are bonded to each other with a water-soluble adhesive therebetween, and the amount of the water-soluble adhesive applied to a unit area of the inner region is larger than that of the adhesive applied to the unit area of the outer peripheral region.

2. The water-decomposable absorbent article as set forth in claim 1, wherein an interlayer peeling rate of constituent layers when wet is higher in the outer peripheral region than in the inner region.

3. The water-decomposable absorbent article as set forth in claim 1, wherein the outer peripheral region has a width of from 2 to 25 mm inwardly from a peripheral edge of the absorbent article.

4. The water-decomposable absorbent article as set forth in claim 1, wherein the solubility in water of the adhesive in the inner region is lower than that of the adhesive in the outer peripheral region.

5. The water-decomposable absorbent article as set forth in claim 1, wherein the adhesives applied in the inner region and in the outer peripheral region are each made of polyvinyl alcohol, the applied amount falls between 10 and 30 $g/m^2$ in the outer peripheral region, and the applied amount falls between 30 and 200 $g/m^2$ in the inner region.

6. A water-decomposable absorbent article comprising a water-decomposable back layer, a water-decomposable and liquid-pervious surface layer, and a water-decomposable absorbent layer sandwiched between the back layer and the surface layer, wherein;

the absorbent article including an outer peripheral region being formed in a predetermined width spaced from a peripheral edge of the absorbent article, and an inner region located inside the outer peripheral region, the absorbent layer and the back layer, and/or the absorbent layer and the surface layer are bonded to each other with a water-soluble or water-swellable adhesive therebetween in the inner region, and an interlayer bonding strength of the layers bonded with the adhesive in the inner region is higher than the interlayer bonding strength of the layers in the outer peripheral region, when both wet and dry, and wherein;

constituent layers in the outer peripheral region are bonded to each other with a water-soluble adhesive therebetween, and the solubility in water of the adhesive in the inner region is lower than that of the adhesive in the outer peripheral region.

7. The water-decomposable absorbent article as set forth in claim 6, wherein an interlayer peeling rate of constituent layers when wet is higher in the outer peripheral region than in the inner region.

8. The water-decomposable absorbent article as set forth in claim 6, wherein the outer peripheral region has a width of from 2 to 25 mm inwardly from a peripheral edge of the absorbent article.

9. The water-decomposable absorbent article as set forth in claim 6, wherein the adhesives applied in the inner region and in the outer peripheral region are each made of polyvinyl alcohol, the applied amount falls between 10 and 30 $g/m^2$ in the outer peripheral region, and the applied amount falls between 30 and 200 $g/m^2$ in the inner region.

* * * * *